(12) United States Patent
Cormier et al.

(10) Patent No.: US 7,184,826 B2
(45) Date of Patent: Feb. 27, 2007

(54) DEVICE AND METHOD FOR ENHANCING TRANSDERMAL FLUX OF AGENTS BEING DELIVERED OR SAMPLED

(75) Inventors: Michel J. N. Cormier, Mountain View, CA (US); Armand P. Neukermans, Palo Alto, CA (US); Barry Block, Los Altos, CA (US); Felix T. Theeuwes, Los Altos Hills, CA (US); Alfred A. Amkraut, Palo Alto, CA (US)

(73) Assignee: Alza Corporation, Mountain View, CA (US)

( * ) Notice: Subject to any disclaimer, the term of this patent is extended or adjusted under 35 U.S.C. 154(b) by 0 days.

(21) Appl. No.: 08/877,155

(22) Filed: Jun. 17, 1997

(65) Prior Publication Data

US 2002/0016562 A1 Feb. 7, 2002

Related U.S. Application Data

(60) Provisional application No. 60/019,990, filed on Jun. 18, 1996.

(51) Int. Cl.
*A61M 1/30* (2006.01)
*A61M 31/00* (2006.01)
*A61B 5/00* (2006.01)

(52) U.S. Cl. .................. 604/21; 604/506; 604/600; 604/575

(58) Field of Classification Search ............ 604/20, 604/21, 264, 272, 891.1, 175, 239, 506; 607/120, 607/126, 127, 128, 130, 131, 152; 600/575, 600/576
See application file for complete search history.

(56) References Cited

U.S. PATENT DOCUMENTS

| 946,837 | A | 1/1910 | Common | |
|---|---|---|---|---|
| 2,893,392 | A | 7/1959 | Wagner et al. | 128/253 |
| 3,072,122 | A | 1/1963 | Rosenthal | 128/253 |
| 3,675,766 | A | 7/1972 | Rosenthal | 206/63.4 |
| 3,814,097 | A | 6/1974 | Ganderton et al. | 128/268 |
| 3,964,482 | A | 6/1976 | Gerstel et al. | 128/260 |
| 4,141,359 | A | 2/1979 | Jacobsen et al. | 128/172.1 |
| 4,250,878 | A | 2/1981 | Jacobsen et al. | 128/207.21 |
| 4,340,048 | A | 7/1982 | Eckenhoff | 128/213 R |
| 4,383,529 | A | 5/1983 | Webster | 604/20 |
| 4,655,766 | A | 4/1987 | Theeuwes et al. | 604/896 |
| H356 | H | * 11/1987 | Stokes et al. | 128/785 |
| 4,711,247 | A | 12/1987 | Fishman | 128/743 |

(Continued)

FOREIGN PATENT DOCUMENTS

EP 0 497 620 A2 8/1992

(Continued)

OTHER PUBLICATIONS

Reiss, Susan M., Biophotonics International, May/Jun. 1997, pp. 43-45, "Glucose- and Blood-Monitoring Systems Vie For Top Spot."

(Continued)

*Primary Examiner*—Sharon Kennedy
(74) *Attorney, Agent, or Firm*—Wilson Sonsini Goodrich and Rosati

(57) ABSTRACT

A percutaneous agent delivery or sampling device comprising a sheet having a plurality of microblades for piercing and anchoring to the skin for increasing transdermal flux of an agent and for improving the attachment of the device to the skin.

24 Claims, 8 Drawing Sheets

U.S. PATENT DOCUMENTS

| | | | | |
|---|---|---|---|---|
| 4,753,651 A | | 6/1988 | Eckenhoff | 424/449 |
| 4,922,926 A | * | 5/1990 | Hirschberg et al. | 128/785 |
| 5,036,861 A | | 8/1991 | Sembrowich et al. | 128/763 |
| 5,080,646 A | | 1/1992 | Theeuwes et al. | 604/20 |
| 5,147,296 A | | 9/1992 | Theeuwes et al. | 604/20 |
| 5,169,382 A | | 12/1992 | Theeuwes et al. | 604/20 |
| 5,169,383 A | | 12/1992 | Gyory et al. | 604/20 |
| 5,250,023 A | | 10/1993 | Lee et al. | 604/20 |
| 5,279,543 A | | 1/1994 | Glikfeld et al. | 604/20 |
| 5,279,544 A | | 1/1994 | Gross et al. | 604/20 |
| 5,300,100 A | * | 4/1994 | Latterell et al. | 607/130 |
| 5,309,909 A | | 5/1994 | Gadsby et al. | 128/639 |
| 5,312,456 A | | 5/1994 | Reed et al. | 411/456 |
| 5,484,399 A | * | 1/1996 | DiResta et al. | 604/21 |
| 5,569,272 A | | 10/1996 | Reed et al. | 606/151 |
| 5,571,162 A | * | 11/1996 | Lin | 607/122 |
| 5,702,359 A | * | 12/1997 | Hofmann et al. | 604/20 |
| 5,800,378 A | * | 9/1998 | Edwards et al. | 604/22 |

FOREIGN PATENT DOCUMENTS

| | | |
|---|---|---|
| FR | 1.133.709 | 4/1957 |
| WO | WO 92/10234 | 6/1992 |
| WO | WO 94/05368 | 8/1992 |
| WO | WO 96/00110 | 1/1996 |
| WO | WO 96/17648 | 6/1996 |
| WO | WO 96/37155 | 11/1996 |
| WO | WO 96/37256 | 11/1996 |
| WO | WO 97/07734 | 3/1997 |
| WO | WO 98/00193 | 1/1998 |

OTHER PUBLICATIONS

Eppstein, Jonathan, et al., "Rapid Transdermal Drug Delivery With Thermal Micro-Poration" presented at a transdermal delivery conference in San Diego on Dec. 15-18, 1997, sponsored by IBC.

\* cited by examiner

DEVICE AND METHOD FOR ENHANCING TRANSDERMAL FLUX OF AGENTS BEING DELIVERED OR SAMPLED

CROSS-REFERENCE TO RELATED APPLICATIONS

A claim is made, under 35 USC 119 (e), to the benefit of the filing of U.S. patent application Ser. No. 60/019,990 filed Jun. 18, 1996.

FIELD OF THE INVENTION

The present invention relates to transdermal agent delivery and sampling. More particularly, this invention relates to the transdermal delivery of agents, such as peptides and proteins, as well as the transdermal sampling of agents, such as glucose, body electrolytes and substances of abuse, such as but not limited to alcohol and illicit drugs. The present invention uses skin-piercing microblades to enhance the transdermal flux of the agents during transdermal delivery or sampling and anchoring elements to assist in retaining the delivery or sampling device in the skin.

BACKGROUND OF THE INVENTION

Interest in the percutaneous or transdermal delivery of peptides and proteins to the human body continues to grow with the increasing number of medically useful peptides and proteins becoming available in large quantities and pure form. The transdermal delivery of peptides and proteins still faces significant problems. In many instances, the rate of delivery or flux of polypeptides through the skin is insufficient to produce a desired therapeutic effect due to the binding of the polypeptides to the skin. In addition, polypeptides and proteins are easily degraded during and after penetration into the skin, prior to reaching target cells. Likewise, the passive flux of water soluble small molecules such as salts is limited.

One method of increasing the transdermal delivery of agents relies on the application of an electric current across the body surface or on "electrotransport". "Electrotransport" refers generally to the passage of a beneficial agent, e.g., a drug or drug precursor, through a body surface such as skin, mucous membranes, nails, and the like. The transport of the agent is induced or enhanced by the application of an electrical potential, which results in the application of electric current, which delivers or enhances delivery of the agent. The electrotransport of agents through a body surface may be attained in various manners. One widely used electrotransport process, iontophoresis, involves the electrically induced transport of charged ions. Electroosmosis, another type of electrotransport process, involves the movement of a solvent with the agent through a membrane under the influence of an electric field. Electroporation, still another type of electrotransport, involves the passage of an agent through pores formed by applying a high voltage electrical pulse to a membrane. In many instances, more than one of these processes may be occurring simultaneously to different extents. Electrotransport delivery generally increases agent delivery, particularly large molecular weight species (e.g., polypeptides) delivery rates, relative to passive or non-electrically assisted transdermal delivery. However, further increases in transdermal delivery rates and reductions in polypeptide degradation during transdermal delivery are highly desirable.

One method of increasing the agent transdermal delivery rate involves pre-treating the skin with, or alternatively co-delivering with the beneficial agent, a skin permeation enhancer. The term "permeation enhancer" is broadly used herein to describe a substance which, when applied to a body surface through which the agent is delivered, enhances its electrotransport flux. The mechanism may involve a reduction of the electrical resistance of the body surface to the passage of the agent therethrough, an increase in the permeability of the body surface, the creation of hydrophilic pathways through the body surface, and/or a reduction in the degradation of the agent (e.g., degradation by skin enzymes) during electrotransport.

There have been many attempts to enhance transdermal flux by mechanically puncturing the skin prior to transdermal drug delivery. See for example U.S. Pat. No. 5,279,544 issued to Gross et al., U.S. Pat. No. 5,250,023 issued to Lee et al., and U.S. Pat. No. 3,964,482 issued to Gerstel et al. These devices utilize tubular or cylindrical structures generally, although Gerstel does disclose the use of other shapes, to pierce the outer layer of the skin. Each of these devices provide manufacturing challenges, limited mechanical attachment of the structure to the skin, and/or undesirable irritation of the skin.

As has been discussed, a variety of chemicals and mechanical means have been explored to enhance transdermal flux. However, there is still a need to provide a device suitable for increasing transdermal flux which device is low-cost and which can be manufactured reproducibly (i.e., without significant variation from device to device) in high volume production and to improve the attachment of the device to the skin.

DESCRIPTION OF THE INVENTION

The present invention provides a reproducible, high volume production, low-cost device suitable for increasing transdermal flux and improving attachment to the skin with minimal to no skin irritation. The device generally comprises a structure that attaches to the skin more effectively than the prior art devices. The invention comprises a plurality of microblades for piercing and anchoring to the skin. The blades typically have a length of less than about 0.4 mm and a width and thickness which is even smaller. In spite of their small size, the blades can be made with an extremely reproducible size and shape so that the microslits formed by the blades puncturing the skin also have a very reproducible size and depth. Because the blades have a small thickness (i.e., small relative to the width and length of the blades), the blades produce less tissue damage for a given cross-section than a skin piercing microneedle having a circular cross-section. The device of the present invention pierces the stratum corneum of a body surface to form pathways through which a substance (e.g., a drug) can be introduced (i.e., delivery) or through which a substance (e.g., a body electrolyte) can be withdrawn (i.e., sampling).

In one aspect of the invention, the device comprises a sheet having a plurality of openings therethrough, a plurality of microblades integral therewith and extending downward therefrom, and means for anchoring the device to a body surface. In the many different aspects of the invention, the device is anchored to the body surface in any of plurality of ways, including but not limited to, having an extension such as a prong or barb extending from at least some of the microblades, having an opening extending perpendicular through at least some of the microblades, covering essentially the entire surface area of the skin contacting surface of the device with adhesive except for one side of the microblades, orienting at least some of the plurality of microblades at an angle of 90° to the remainder of the plurality of microblades, orienting at least some of the plurality of microblades at an angle within a range of about 1° to about 89° with respect to the remainder of the plurality of microblades, providing a plurality of second openings through the sheet which make the device more shapeable with respect to the body surface. The device of the present invention can be used in connection with drug delivery, body analyte or drug sampling, or both. Delivery devices for use with the present invention include, but are not limited to, electrotransport devices, passive devices, osmotic devices and pressure-driven devices. Sampling devices for use with the present invention include, but are not limited to, "reverse" electrotransport devices as disclosed in Glikfeld et al., U.S. Pat. No. 5,279,543, passive devices, osmotic devices and negative pressure driven devices.

The present invention also provides a high yield, low-cost method for producing, in extremely reproducible fashion, the device of the present invention.

MODES FOR CARRYING OUT THE INVENTION

Figure 1:
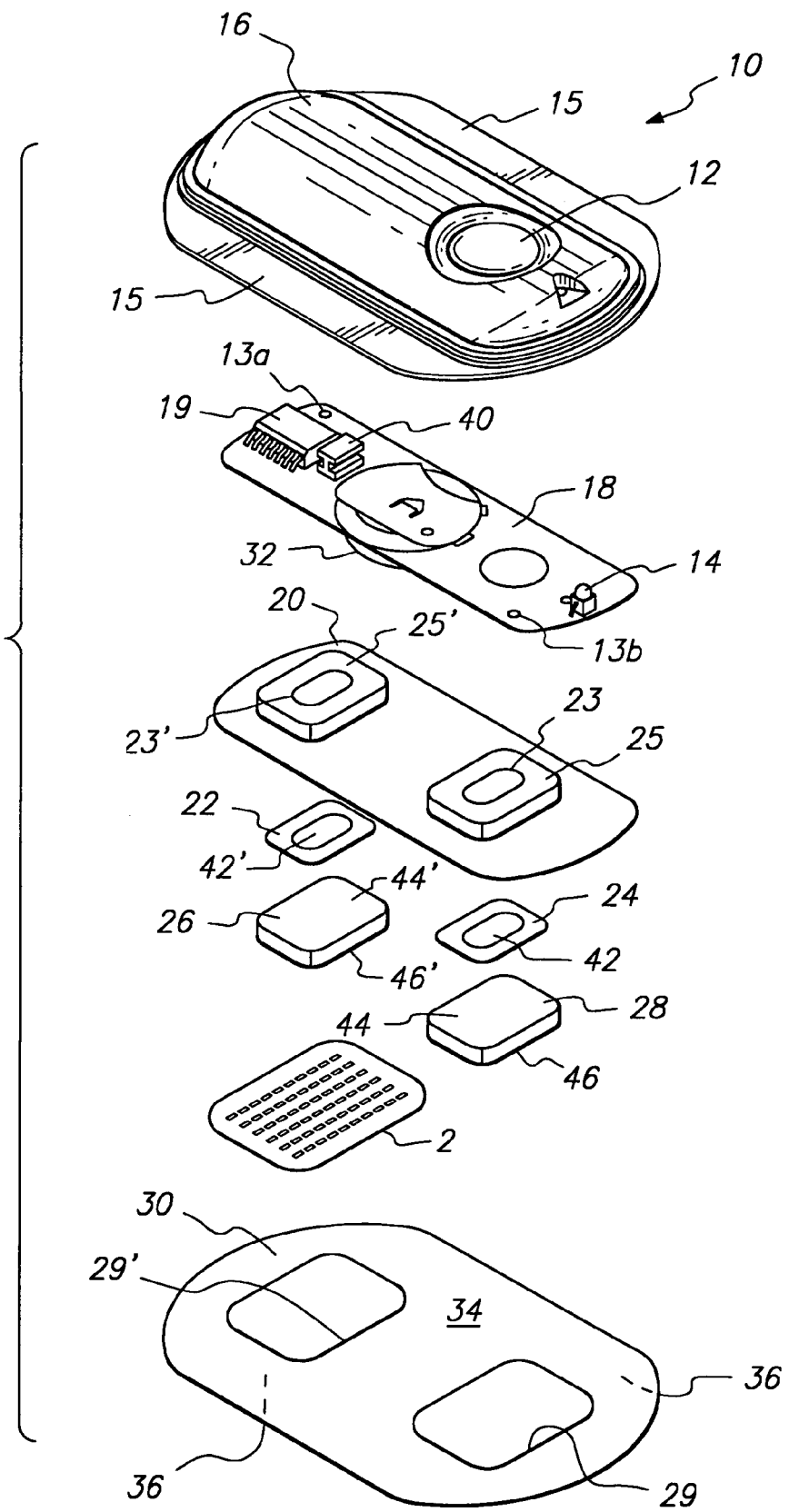
FIG. 1 is a perspective exploded view of one embodiment of an electrotransport agent delivery system with a blade array device according to one embodiment of the present invention.

Turning now to the drawings in detail, one embodiment of the device 2 of the present invention is generally shown in FIG. 1 for use with electrotransport delivery device 10. Device 2 is used for the percutaneous administration or sampling of an agent. The terms "substance", "agent" and "drug" are used interchangeably herein and broadly include physiologically or pharmacologically active substances for producing a localized or systemic effect or effects in mammals including humans and primates, avians, valuable domestic household, sport or farm animals, or for administering to laboratory animals such as mice, rats, guinea pigs, and the like. These terms also include substances such as glucose, electrolyte, alcohol, illicit drugs, etc. that can be sampled through the skin. The major barrier properties of the skin, such as resistance to drug penetration, reside with the stratum corneum. The inner division of the epidermis generally comprises three layers commonly identified as stratum granulosum, stratum Malpighi, and stratum germinativum. Once a drug penetrates below the stratum corneum, there is substantially less resistance to permeation through the underlying stratum granulosum, stratum Malpighi, and stratum germinativum layers for absorption and circulation of drug into the body. The device of the present invention is used to form microslits in the stratum corneum and produce a percolation area in the skin for improved transdermal delivery or sampling of an agent.

Figure 2:
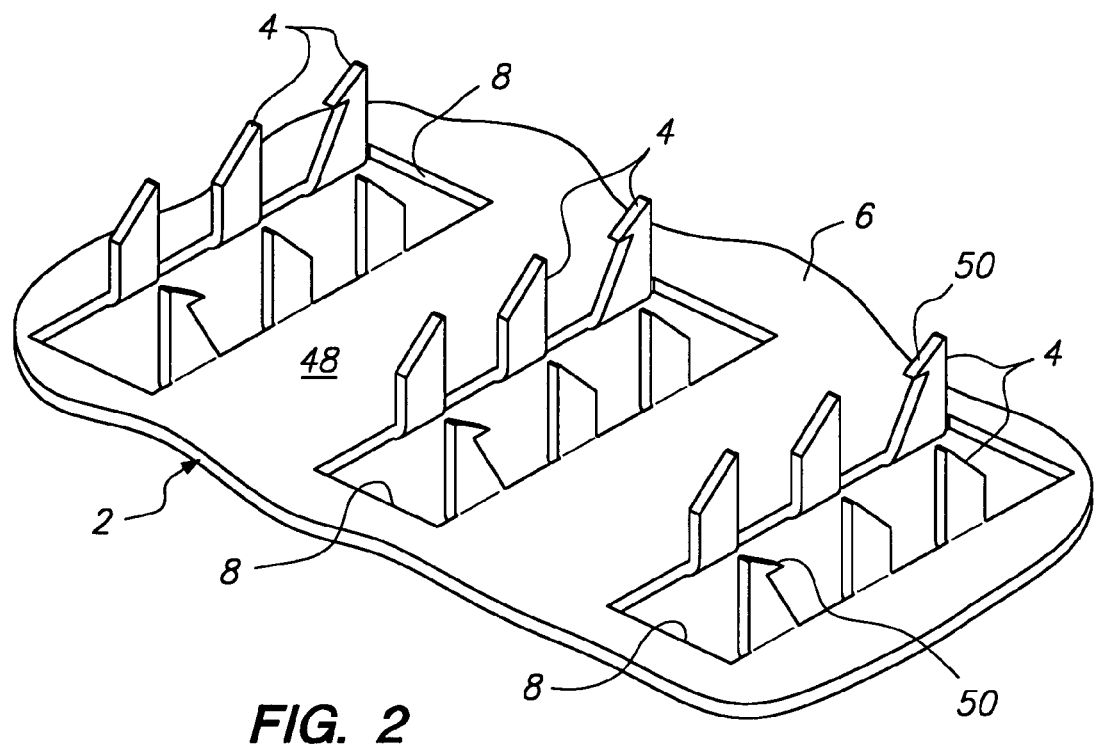
FIG. 2 is an enlarged perspective view of the skin proximal side of the blade array device in accordance with one embodiment of the present invention.

Device 2 comprises a plurality of microblades 4 (i.e., a blade array) extending downward from one surface of a sheet or plate 6 (see FIG. 2 in which device 2 is in an inverted position to show the microblades). As seen best in FIG. 2, the microblades are of a substantially identical and uniform configuration. The microblades 4 penetrate the stratum corneum of the epidermis when pressure is applied to the device to increase the administration of or sampling of a substance through a body surface. The term "body surface" as used herein refers generally to the skin, mucous membranes, and nails of an animal or human, and to the outer surface of a plant.

Furthermore, the device 2 of the present invention improves the attachment of the device to the skin so that the percolation areas and a continuous pathway are preserved during movement of the body surface. In the embodiment shown in FIG. 2, projections in the form of barbs 50 on at least one of the blades 4 assist in anchoring the device 2 and any corresponding device or structure used in combination therewith to the skin. Barbs 50 can be on any number of the blades from one blade to all blades. Other embodiments which assist to anchor the device to the skin will be discussed below.

The microblades 4 are generally formed from a single piece of material and are sufficiently sharp and long for puncturing the stratum corneum of the skin. In one embodiment, the microblades 4 and the sheet 6 are essentially impermeable or are impermeable to the passage of an agent. The sheet 6 is formed with an opening 8 between the microblades 4 for enhancing the movement of an agent therethrough. In the case of therapeutic agent (e.g., drug) delivery, the drug is released from a drug-containing reservoir (not shown in FIG. 2) through microslits formed by the microblades 4 cutting through the stratum corneum, migrating down the outer surfaces of the microblades and through the stratum corneum to achieve local or systemic therapy. In the case of agent (e.g., body analyte) sampling, the analyte (or interstitial fluid containing the analyte) migrates from the body through the microslits in the stratum corneum which are cut by the microblades 4. In one embodiment, the opening 8 corresponds to the portion of the sheet 6 occupied by each of the microblades prior to the blades being transpositioned into the downward depending position. The number of microblades 4 per opening 8 can be any number, preferably however between 1 and about 30 blades per opening. Furthermore, the number of openings per device and the number of blades per device are independent. The device may have only one opening and one microblade. The agent can be administered at a controlled rate of release from the reservoir through an agent release rate controlling material (not shown) covering the openings 8.

As is best shown in FIG. 2, the microblades 4 have a thickness which is much smaller than the width of the blades near their base, i.e., near the point where the blades are attached to the plate 6. This blade geometry provides maximum drug percolation area with a minimum blade penetration area, and hence less tissue damage. The drug percolation area is the skin area in contact with the blades which provides for drug penetration in the skin. The microblades are shaped with the largest possible surface area with a minimal cross-sectional area so as to give the largest possible percolation area. Thin microblades are better than round protrusions for this purpose because for the same cross-section, a thin blade produces more percolation area and less tissue damage than a round protrusion. This is a crucial advantage over the prior art round elements such as needles and tubes. Thin microblades also require less insertion force than round protrusions. The width of each blade can be any of a range of widths. The widths can be different from blade to blade in the array pattern. Likewise, the width can be variable along the length of the blade, as will be described in more detail below. The width of the blade at the intersection of the blade and the body surface after the blade array has been inserted is preferably in the range of about 25 µm to about 500 µm, more preferably about 50 µm to about 400 µm, more preferably 100 µm to about 300 µm.

Figure 5:
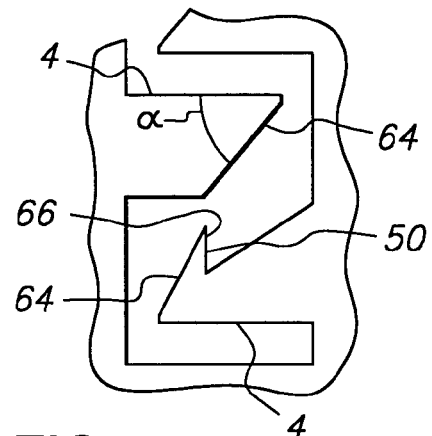
FIG. 5 is an enlarged view of a portion of the blades of the blade array pattern of FIG. 3.

In one embodiment, the microblades 4 (FIG. 5) are also provided with slanted (i.e., angled) leading edges 64 to further reduce the insertion force required to press the blades into the skin tissue. The angle of the leading edge is designated as α. The slanted leading edges produce a cut through the skin tissue that is equal to the full width of the blade 4 while reducing the amount of metal that is in the skin tissue. In other words, a flat leading edge (i.e., α is 90°) produces a blade with a larger amount of blade material in the skin tissue than is produced by a blade having a slanted leading edge. The leading edges of each blade can all be the same angle or can be at different angles as shown in FIG. 5. The angle α of each leading edge can be any angle between about 10° to 90°, preferably between about 10° to 60°, more preferably about 10° to 40°. The leading edge can also be segmented into two sections at different angles. For example, the first segment can have an angle α between about 10° to 40° and then transition to a second segment having an angle between 20° to 60°. Alternatively, the leading edge of each blade can be arcuate (i.e., curved) in shape, having, for example, a convex or concave shape. In one embodiment, the leading edge is a curved tip across the entire width of the blade.

The microblades 4 are formed using a photo-etching process which is described in detail hereinafter. This process allows the microblades 4 to be reproducibly formed on a very small (i.e., tens of microns) scale. This process also allows the microblades 4 to be formed in shapes which help anchor device 2 to the skin. In one embodiment, the microblades 4 are provided with barbs 50 (FIGS. 2, 3 and 5) in some fashion so that the device 2 and any corresponding device attached thereto stays attached to the skin after being applied with pressure. The degree of attachment and the number and size of the barbs is such as to retain the delivery or sampling device during the normal activity of the wearer, but not cause pain upon removal. As the microblades are pressed into the skin tissue for use, the leading edge 64 of each microblade cuts through and pushes aside the skin tissue. After the microblades have come to rest in the skin, the skin due to its elastic nature at least partially comes back together around the edges of the microblades, in this way the surface 66 on each microblade having a barb 50 engages skin tissue and anchors the device in the skin. If the blade is left in the skin for an extended period of time (e.g., 24 hours), the skin tissue begins to heal together in the area behind the surface 66 of the barb thus improving the anchoring of the device. Only one barb per blade is shown in the figures but it is within the scope of the present invention that each blade can have a plurality of barbs extending therefrom. The microblades, in one embodiment, have a cross-section that is wider in the area of the skin distal end of the blade than in the area of the skin proximal end, thus providing additional anchoring of the distal end in the skin. For example, the blades can have an "arrowhead" shape. Furthermore, the barbs 50 shown in the figures are in the same plane as the blade, however the barbs can be oriented outside of that plane for example by a separate bending step or by using a shaped punch and die to produce a curve in the blade and barb. Curving the tips of the blade outside the plane of the blade generally provides better anchoring. Insertion of such blades causes the barbs to curve in the curve direction but retraction causes them to return to their prior position. The resulting curved cross-section of the blade can be, but is not limited to, angular, semi-circular, C-shaped, or banana-shaped to effect a larger cross-section of openings in the skin.

Figure 3:
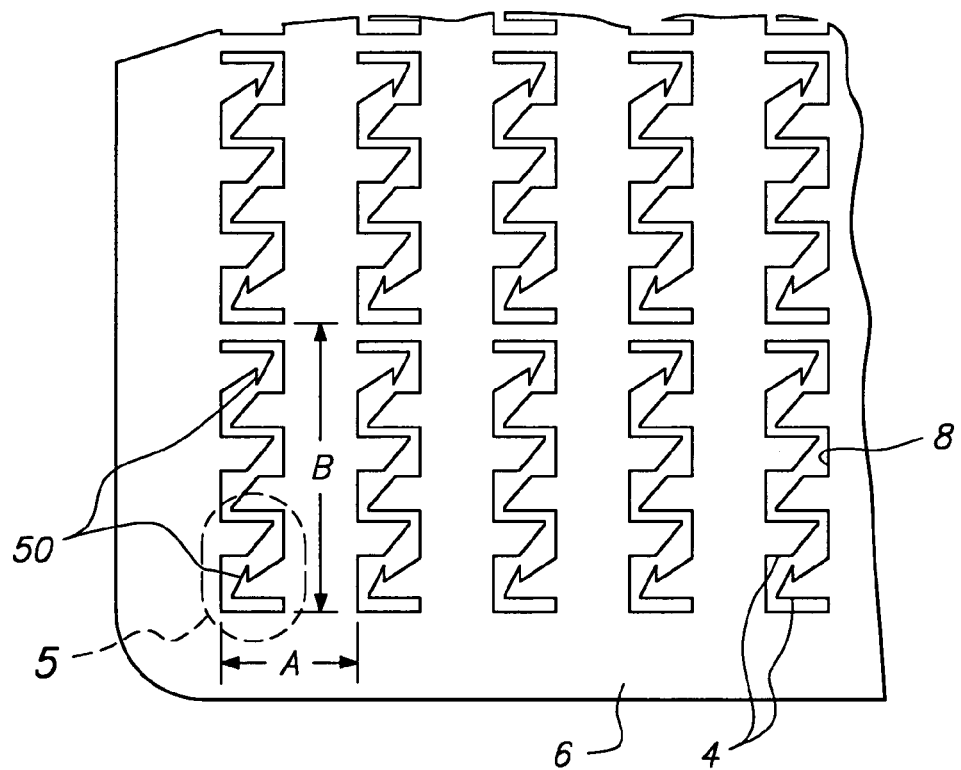
FIG. 3 is a partial top plan view of a blade array pattern in accordance with one embodiment of the present invention for forming blades with anchoring elements.

The plurality of microblades 4 for puncturing the stratum corneum are present on one face surface 48 of the device 2 in any predetermined arrangement, for example, as a cluster of blades spaced in rows having any desired number, or in any spaced apart relation of one blade to each other. The device 2 of the embodiment shown in FIGS. 1 and 2 is produced by the pattern shown in FIG. 3. Each blade has a width and thickness that facilitates penetration of the stratum corneum without bending. In the embodiment of FIG. 3, there are six blades 4 in each opening 8 in sheet 6. Each opening 8 in this embodiment is 1 mm long and 300 μm wide. Correspondingly, the width of each blade is between about 137.5 μm to about 175 μm and the length is about 250 μm. The required length of the blades is subject to variation of the body surface being penetrated and corresponds to the natural thickness of the stratum corneum, for one of the principle features of the invention is that the blades are to penetrate the stratum corneum into the epidermis. Usually, the blades will be about 25 μm to about 400 μm in length, with the length for most applications being between about 50 μm to about 200 μm.

Figure 8:
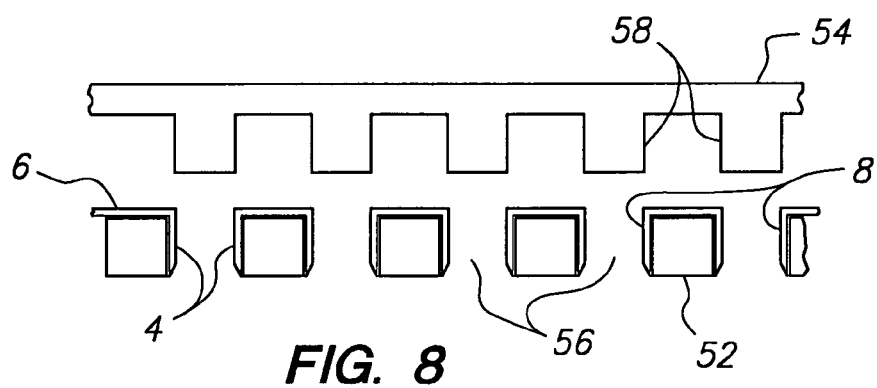
FIG. 8 is a diagrammatic representation of a method for producing blades of the present invention from the blade array pattern of FIG. 3.

The pattern for any of the blade array devices of the present invention are produced with a photo-etching process. A thin sheet or plate 6 of metal such as stainless steel or titanium is etched photo-lithographically with patterns containing blade-like structures. In general, a thin laminate dry resist or wet resist is applied on a sheet about 7 μm to about 100 μm thick, preferably about 25 μm to about 50 μm thick. The resist is contact exposed using a mask having the desired pattern and is subsequently developed. These operations are conducted in much the same way that they are for the manufacture of a printed circuit board. The sheet is then etched using acidic solutions. After the pattern has been etched through the sheet, the sheet is placed on a die 52 (shown schematically in FIG. 8) having a plurality of openings 56 corresponding to the openings 8 in the sheet. A punch 54 having a plurality of protrusions 58 corresponding to the openings in the sheet and die is initially located above the sheet and die. At the initial stage, the blades 4 are in the same plane as the rest of the sheet 6. The protrusions 58 on the punch 54 are then pressed into the openings 56, thus bending the blades 4 downward to be at an angle (e.g., substantially perpendicular) to the plane of the sheet. The finished structure provides blades 4 with an adjacent opening 8 for the passage of a substance therethrough when the device 2 is applied to the skin. Rectangular openings 8 are shown in the figures but the invention encompasses the use of any shape openings including, but not limited to, square, triangular, circular and elliptical.

Figure 4:
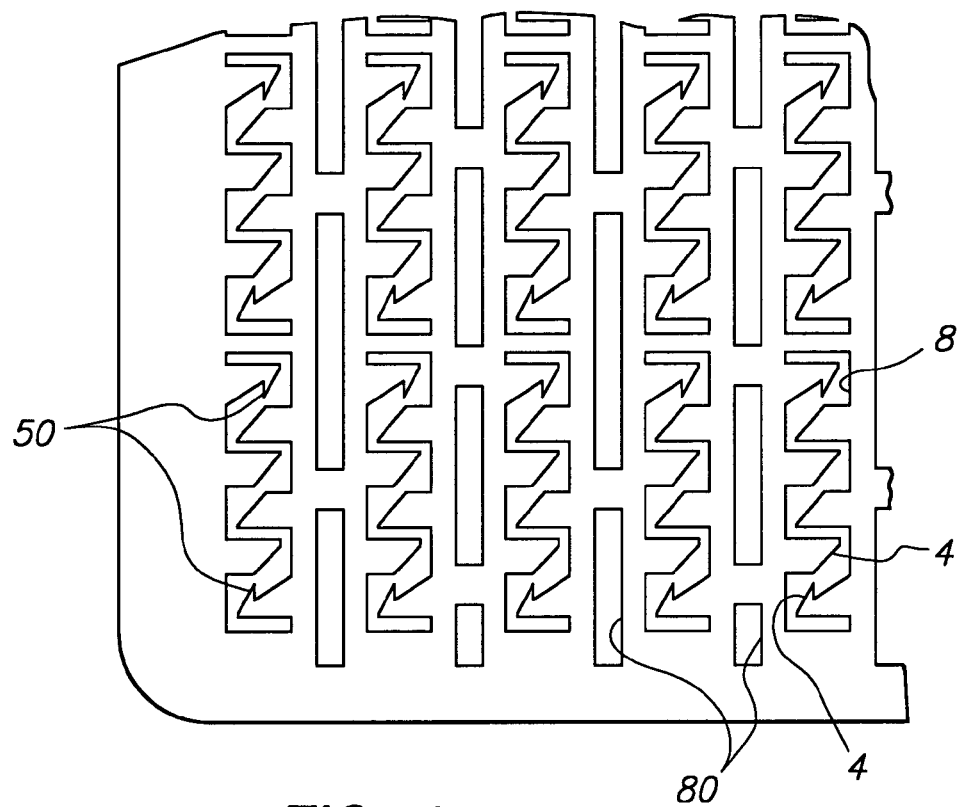
FIG. 4 is partial top plan view of yet another embodiment of the blade array pattern of FIG. 3.

The sheet 6 in some areas can have additional etched openings 80 (FIG. 4) to alleviate the curl created during punching and/or to provide for flexibility in the dense blade array patterns because in some embodiments the sheet becomes very stiff after punching. The openings can be any of a variety of shapes (e.g., rectangular, circular, elliptical, triangular, etc.) The openings also allow the sheet to be more easily curved to match the curvature of the body surface to which it is to be attached which improves anchoring of the device. The present invention maximizes the openings through the sheet but with a sufficient number of horizontal and vertical continuous portions in the sheet to prevent the sheet from being too flexible (i.e., flimsy). If the openings are made too long in any one dimension, the sheet will bend (i.e., crinkle). In addition, it is also possible to treat the devices after punching with heat or plastic deformation such that the radius of curvature of the sheet becomes equal to or somewhat smaller than the curvature of the body, where it is to be attached to enhance anchoring. The concave surface can be shaped to match the convex pattern of the body.

Figure 6:
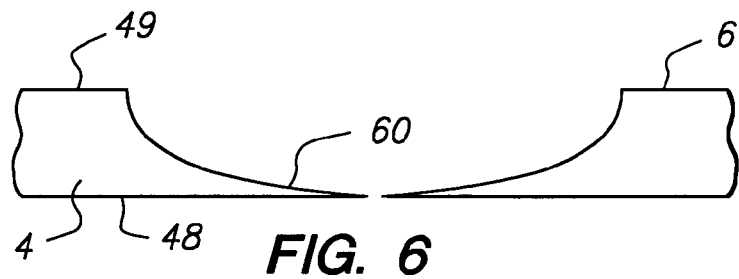
FIG. 6 is an enlarged view of a blade tip in accordance with one embodiment of the present invention.
Figure 7:
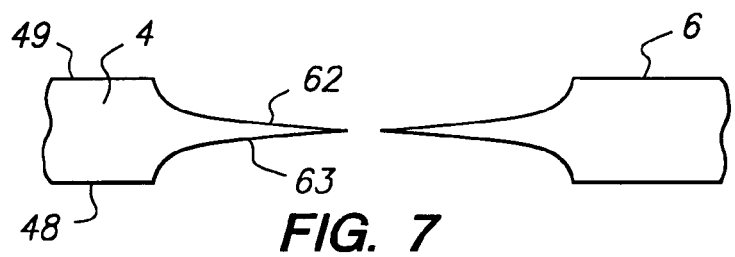
FIG. 7 is an enlarged view of a blade tip in accordance with another embodiment of the present invention.

The blades 4 can be patterned with resist on both sides 48,49 and subsequently etched simultaneously from both sides (FIG. 7) to achieve maximum pattern resolution for a given sheet thickness and to produce a knife-like edge that can not be achieved with conventional stamping and punching processes. Alternatively, the blades 4 can be patterned and etched from one side (i.e., side 49) only (FIG. 6). When etching from one side only, the etching process can be controlled to etch selective depths in the plate 6 along the length of the blades (e.g., at the blade tips) to produce a single angle 60 at the tip of the blade which maximizes the sharpness of the knife-like edge of the blade. In this embodiment, the lithography process produces a portion of the blade that is thinner than the remainder of the thickness of the blade and of the sheet. The lithography process also can produce very small dimensioned elements for the anchoring and the penetration aspects of the invention.

In another embodiment of the two-sided etching process, the blade array pattern of any of the embodiments of the present invention is etched into the top surface 49 of sheet 6. A second pattern equivalent to the area bounded by each of the openings 8 (e.g., rectangular) is etched into the bottom surface 48 such that each of the blades in the blade array pattern is thinner than the surrounding sheet 6. As a result, the sheet 6 forms a strong base and as the punch 54 deforms the blades 4 downward, each of the blades plastically deforms so as to produce blades that are straighter and more truly perpendicular to the sheet.

In one embodiment of the etching process, a dry resist (e.g., "Dynachem FL" available from Dynachem located in Tustin, Calif.) is applied 12.5 μm thick to one or both sides of the sheet and exposed in a standard manner. Then a suitable spray etcher (e.g., "Dynamil VRP 1 0/NM" available from Western Tech. Assoc. located in Anaheim, Calif.) is used to spray) a mixture of ferric chloride and hydrochloric acid onto the resist and sheet at 52° C. (125° F. for two minutes. A standard caustic stripper is used for the resist removal.

In another embodiment of the etching process, a wet resist (e.g., "Shipley 111S" available from Shipley Corporation, located in Marlborough, Mass.) is applied 7.5 μm thick at about 20° C. (70° F.) to one or both sides of the sheet and exposed in a standard manner. Then a suitable etchant (e.g., ferric chloride) is sprayed onto the resist and sheet at 49° C. (120° F.). A standard caustic stripper is used for the resist removal.

Figure 9:
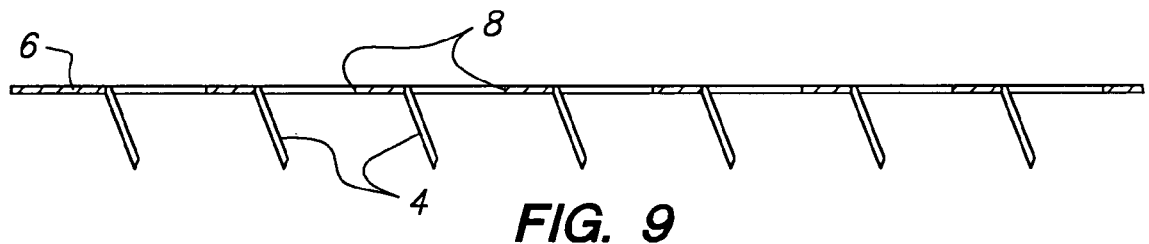
FIG. 9 is an enlarged cross-sectional view of angled blades in accordance with one embodiment of the present invention.

Generally, the blades 4 are at an angle of about 90° to the surface 48 of the sheet 6 after being punched, but they can be disposed at any angle forward or backward from the perpendicular position that will facilitate penetration of and attachment to the stratum corneum. In one embodiment (FIG. 9), the blades are all aligned at an angle between about 1° and about 89° degrees, preferably about 10° to about 60°, more preferably about 20° to 45° to facilitate the device being slid along and into the skin. The angled blades have two principal advantages. First, penetration of the blades is not opposed by the elasticity of the skin because the blades are slid horizontally into the skin as opposed to pressing vertically on the skin. Second, the angled blades act to anchor the device in the skin as any motion of the skin is less likely to dislodge the blades. In addition, other anchoring elements such as barbs, openings, etc. can be used with the angled blades to further enhance anchoring of the device.

Figure 29:
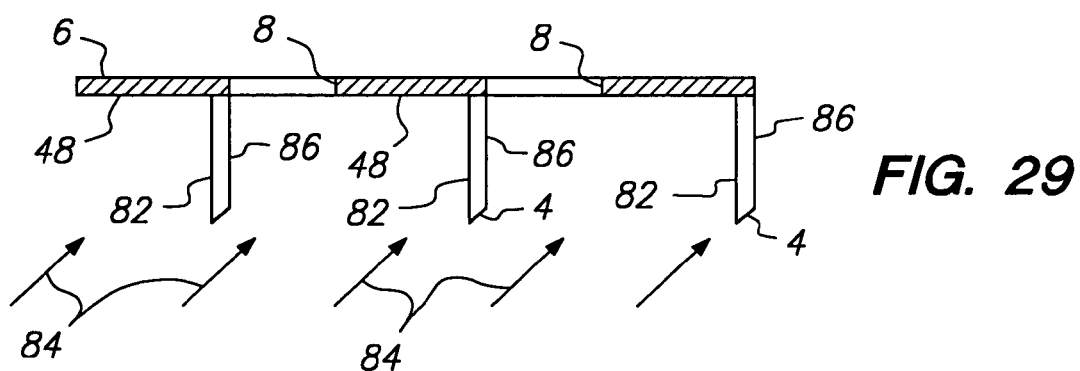
FIG. 29 is a diagrammatic cross-sectional view of another embodiment of the blades of the present invention.

In one embodiment (FIG. 29), anchoring of the device is achieved by coating the surface 48 of sheet 6 and surface 82 of each blade 4 with an adhesive. One method of producing this embodiment comprises spraying the adhesive on the device 2 along the direction indicated by arrows 84. In this embodiment, the agent is free to pass through the openings 8 and along surface 86 of each blade unencumbered by the adhesive. It is also possible to apply the adhesive on only surface 48 and not on the blade surfaces 82. This can be accomplished, for example, by applying the adhesive onto surface 48 after the blades 82 have been punched by spraying the adhesive in a direction which is parallel to the axis of the blades 82. It is further possible to apply the adhesive only on the blade surfaces 82 and not on the surface 48 of sheet 6 in order to anchor the device, although this last design is the least preferred adhesive anchoring means.

The sheet and blades can be made from materials that have sufficient strength and manufacturability to produce blades, such as, glasses, ceramics, rigid polymers, metals and metal alloys. Examples of metals and metal alloys include but are not limited to stainless steel, iron, steel, tin, zinc, copper, platinum, aluminum, germanium, nickel, zirconium, titanium and titanium alloys consisting of nickel, molybdenum and chromium, metals plated with nickel, gold, rhodium, iridium, titanium, platinum, and the like. An example of glasses include a devitrified glass such as "Photoceram" available from Corning in Corning, N.Y. Examples of rigid polymers include but are not limited to polystyrene, polymethylmethacrylate, polypropylene, polyethylene, "Bakelite", cellulose acetate, ethylcellulose, styrene/acrylonitrile copolymers, stryrenetbutadiene copolymers, acrylonitrile/butadiene/styrene (ABS) copolymers, polyvinyl chloride and acrylic acid polymers including polyacrylates and polymethacrylates.

Very dense patterns can be created with unit cells wherein a unit cell has a width A and a length B as illustrated in FIG. 3. In one embodiment (not shown), the pattern has the following characteristics: a unit cell area of 0.63 mm by 3.8 mm; the lineal length of a cut in a unit cell is approximately equal to 15 mm; and the open skin length per square centimeter is 625 mm.

The microblades of the present invention make an elongated, thin microcut (i.e., a slit) in the skin surface because the blades have a small thickness (relative to their width and length) resulting in a minimal blade cross-sectional area for the portions of the blade in the skin. The geometry of the microblades 4 results in minimal blade volume in the skin with maximal blade surface area in the skin. The advantages of the present invention include, but are not limited to: (1) the thin blade geometry produces the maximum drug percolation area for a given cross-section of the blade; (2) minimal tissue damage occurs because the amount of blade material in the skin and hence the volume loading is minimized; (3) slanted leading edges (or equivalent pointed shapes) further minimize the amount of volume loading or tissue damage while preserving a large percolation area; (4) for a given volume loading, the larger the surface area, the larger the frictional retaining force in the skin; and (5) for a given desired percolation area, there are fewer blades necessary and therefore the force on each tip is higher making skin penetration easier.

Figure 10:
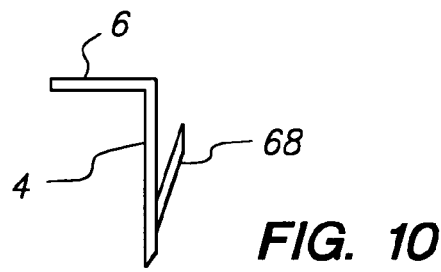
FIGS. 10, 11 and 12 are yet other embodiments of the blades with anchoring elements of the present invention.
Figure 13:
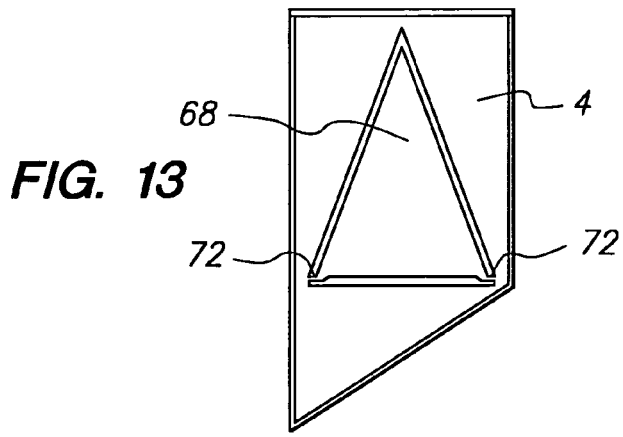
FIG. 13 is a right side elevational view of another embodiment of a blade with an anchoring element.
Figure 14:
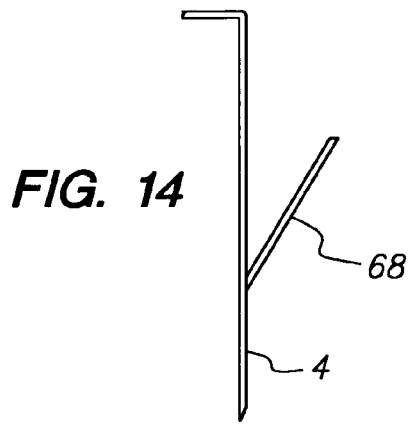
FIG. 14 is an end view of the blade of FIG. 13.
Figure 15:
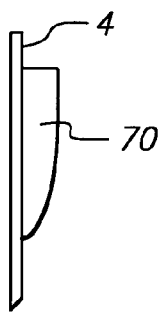
FIGS. 15 and 16 are another embodiment of the blade and an anchoring element.
Figure 16:
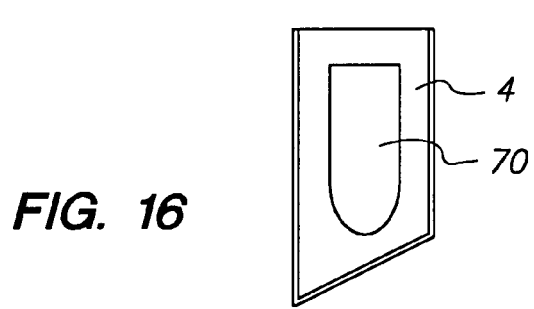

In other embodiments (FIGS. 10–16) other anchoring elements are used in the present invention. In the embodiments shown in FIGS. 10–14, prong 68 is etched in the side of some or all of the blades 4, and punched lightly so as to protrude outward from the plane of each of the blades, as illustrated in FIGS. 10 and 14. After the punching of the prongs, the blades may be repunched to regain their substantially vertical orientation. Hinges 72 (FIG. 13) can be used to control the retention force of the barb for anchoring. The hinges allow for the retention force to be tailored independently of the size of the blade because the force required to bend or punch the prong is set independently of the size of the blades by the shape or size of the hinge. In other words, the force can be tailored by the amount of attachment of the prong to the plate, the greater the attachment, the greater the force.

Figure 11:
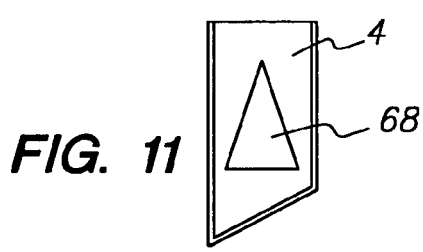
Figure 12:
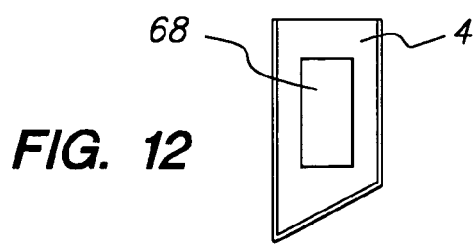

Prongs may protrude from either side of the blade, or both sides, if desired. The shape of each prong can be any of a variety of shapes such as triangular, square, etc. as shown in FIGS. 11 and 12. In another embodiment, a curved protrusion 70 (FIGS. 15 and 16) is made by etching a slit in some or all of the blades followed by punching. The prongs and curved protrusions act to anchor the device in the skin similar to the manner described previously.

Figure 17:
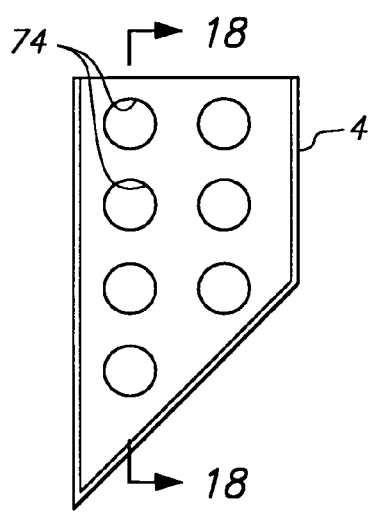
FIG. 17 is a right side elevational view of a blade with anchoring elements in accordance with one embodiment of the present invention.
Figure 18:
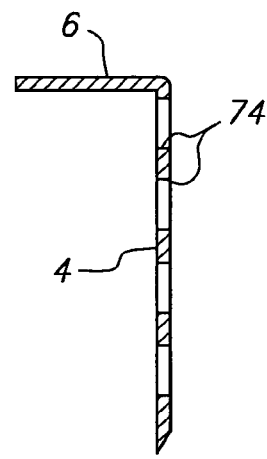
FIG. 18 is a cross-sectional view taken along line 18—18 of FIG. 17.
Figure 19:
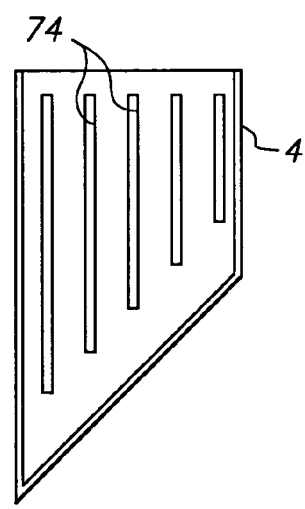
FIG. 19 is a right side elevational view of another embodiment of a blade with an anchoring element.

In other embodiments other anchoring elements are used. In the embodiments of FIGS. 17–19, the blade 4 has additional openings 74 extending through the blade to enhance anchoring. The edges forming the holes or other linear openings are etched through the blade. Alternatively, or in addition, numerous small pits (i.e., indentations) rather than holes can be etched in the surface of the blade. As described above, the elastic nature of the skin tissue causes the skin to move into the openings or pits. In the embodiments with openings, the skin tissue may heal and reconnect through the openings to provide even greater anchoring.

Figure 20:
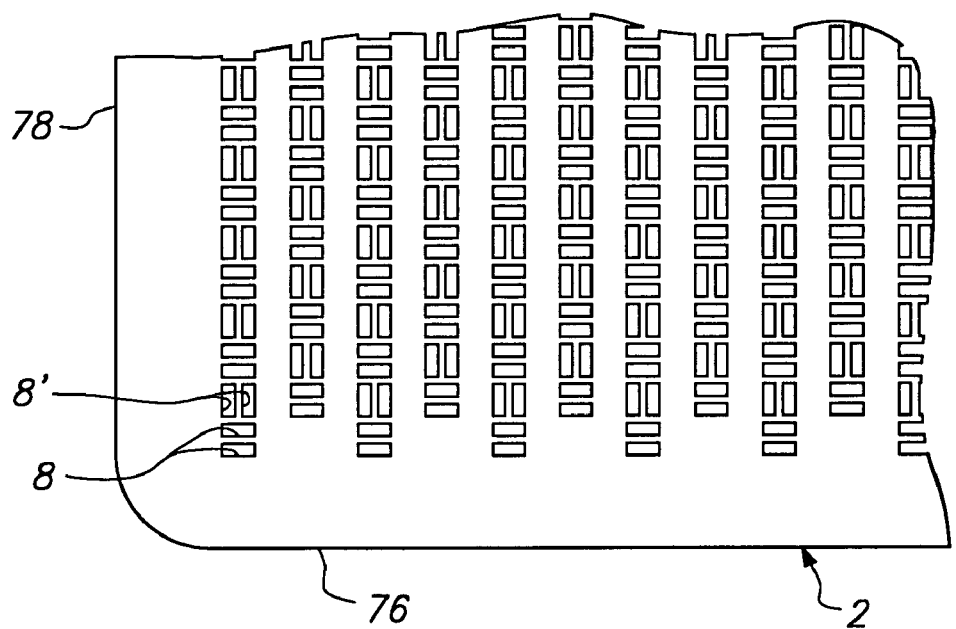
FIG. 20 is an enlarged partial top plan view of still another embodiment of the blade array pattern.
Figure 21:
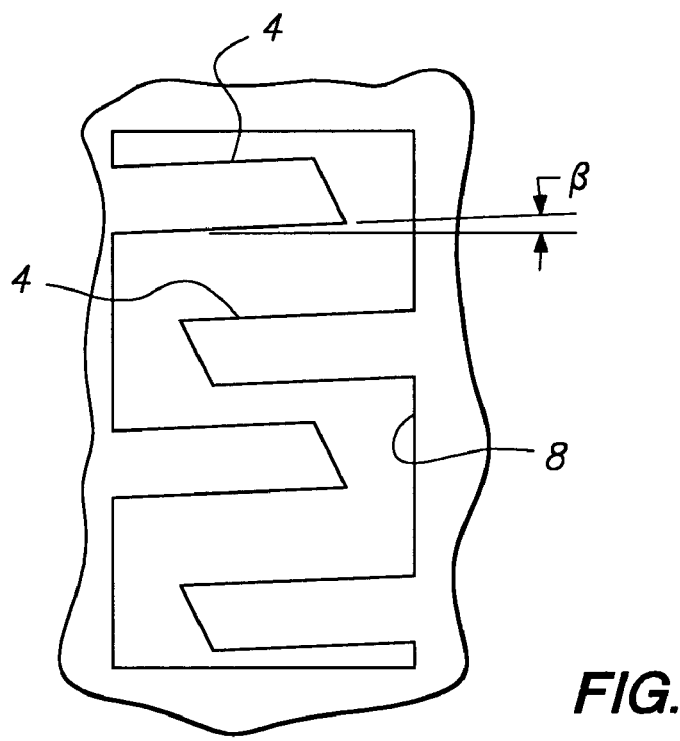
FIG. 21 is an enlarged partial top plan view of yet another embodiment of the blade array pattern.
Figure 22:
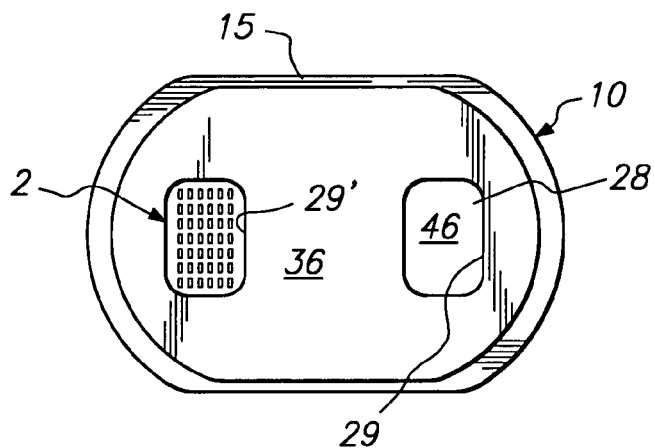
FIG. 22 is a bottom plan view of the electrotransport agent delivery system of FIG. 1.
Figure 23:
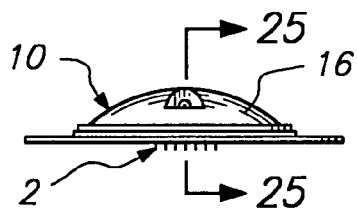
FIG. 23 is a right side elevational view of the electrotransport agent delivery system of FIG. 1.
Figure 24:
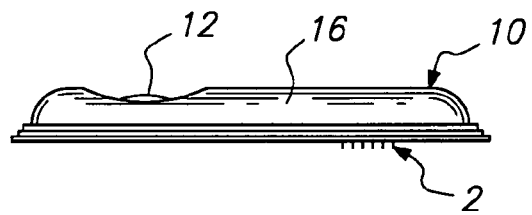
FIG. 24 is a rear elevational view of the electrotransport agent delivery system of FIG. 1.
Figure 25:
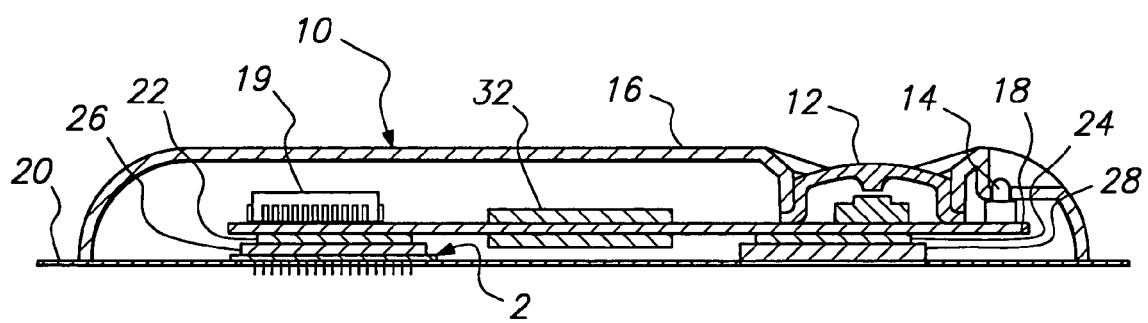
FIG. 25 is a cross-sectional view taken along line 25—25 of the assembled electrotransport agent delivery system of FIG. 23.

In a further embodiment (FIG. 20), a plurality of blades in an opening 8 are arranged at 90° to another plurality of blades in an opening 8' such that anchoring in two directions is obtained. In other words, the blades (not shown) associated with the openings 8 are oriented parallel to the edge 76 of the device 2 and the blades (not shown) associated with the openings 8' are oriented parallel to the edge 78 of the device. The blades associated with each opening 8 can be oriented at any angle with respect to the blades associated with each opening 8'. Alternatively, the blades within each opening can be along perpendicular sides of the openings. In a similar manner, the blades within each opening can be formed in a serrated pattern as illustrated in FIG. 21. This pattern allows the blades to have different, controllable angles with respect to each other defined by the angle of the punch used and the etched angle β of the pattern.

The number of blades and openings of any of the embodiments of the device 2 is variable with respect to the desired flux rate, agent being sampled or delivered, delivery or sampling device used (i.e., electrotransport, passive, osmotic, pressure-driven, etc.), and other factors as will be evident to one of ordinary skill in the art. In general, the larger the number of blades per unit area (i.e., the blade density), the more distributed is the flux of the agent through the skin because there are a greater number of agent-conveying pathways through the skin. Consequently, the smaller the number of blades per unit area, the more concentrated is the flux of the agent through the skin because there are fewer pathways. The present invention has a blade density of at least about 10 blades/cm$^2$ and less than about 1000 blades/cm$^2$, preferably at least about 600 blades/cm$^2$, more preferably at least about 800 blades/cm$^2$. In similar fashion, the number of openings per unit area through which the agent passes is at least about 10 openings/cm$^2$ and less than about 1000 openings/cm$^2$. In one embodiment, the present invention produces a percolation area of about 0.005 to 0.05 cm$^2$/cm$^2$ of body surface, preferably about 0.01 cm$^2$/cm$^2$ of body surface.

One embodiment of the present invention relies on the application of an electric current across the body surface or "electrotransport". Electrotransport refers generally to the passage of a beneficial agent, e.g., a drug or drug precursor, through a body surface such as skin, mucous membranes, nails, and the like. The transport of the agent is induced or enhanced by the application of an electrical potential, which results in the application of electric current, which delivers or enhances delivery of the agent or, for "reverse" electrotransport, samples or enhances sampling of the agent. The electrotransport of the agents into or out of the human body may be attained in various manners. One widely used electrotransport process, iontophoresis, involves the electrically induced transport of charged ions. Electroosmosis, another type of electrotransport process involved in the transdermal transport of uncharged or neutrally charged molecules (e.g., transdermal sampling of glucose), involves the movement of a solvent with the agent through a membrane under the influence of an electric field. Electroporation, still another type of electrotransport, involves the passage of an agent through pores formed by applying an electrical pulse, a high voltage pulse, to a membrane. In many instances, more than one of these processes may be occurring simultaneously to different extents. Accordingly, the term "electrotransport" is given herein its broadest possible interpretation, to include the electrically induced or enhanced transport of at least one charged or uncharged agent, or mixtures thereof, regardless of the specific mechanism(s) by which the agent is actually being transported.

It will be appreciated by those working in the field that the present invention can be used in conjunction with a wide variety of electrotransport drug delivery systems, as the invention is not limited in any way in this regard. For examples of electrotransport drug delivery systems, reference may be had to U.S. Pat. No. 5,147,296 to Theeuwes et al., U.S. Pat. No. 5,080,646 to Theeuwes et al., U.S. Pat. No. 5,169,382 to Theeuwes et al., and U.S. Pat. No. 5,169,383 to Gyory et al., the disclosures of which are incorporated by reference herein in their entirety.

Electrotransport devices generally use at least two electrodes which are in electrical contact with some portion of the skin, nails, mucous membranes, or other body surface. In the case of transdermal agent delivery, one of the two electrodes is commonly referred to as the "donor" or "active" electrode, and is the one from which the agent is delivered into the body. In the case of transdermal agent sampling, one of the two electrodes is referred to as the "receptor" electrode, and is the one into which the agent (e.g., body electrolyte) is collected upon being withdrawn from the body. The second electrode is typically termed the "counter" or "return" electrode, and serves to close the electrical circuit through the body. For example, when the agent to be delivered is a cation, i.e., a positively charged ion, the anode becomes the active or donor electrode, while the cathode serves to complete the circuit. Alternatively, if the agent to be delivered is an anion, i.e., a negatively charged ion, the cathode is the donor electrode. When the agent to be sampled is a cation, the cathode becomes the receptor electrode while the anode serves to complete the circuit. When the agent to be sampled is an anion, the anode becomes the receptor electrode while the cathode serves to complete the circuit. When the agent to be sampled has no net charge (e.g., glucose), then either the anode, or the cathode, or both electrodes, can serve as the receptor electrode. Both the anode and cathode may be donor electrodes if both anionic and cationic agents are delivered simultaneously. Electrotransport delivery systems generally require at least one reservoir or source of the agent to be delivered to the body. Electrotransport sampling systems likewise require at least one reservoir in which to collect the agent being sampled. Examples of such reservoirs include a pouch or cavity as described in U.S. Pat. No. 4,250,878 to Jacobsen, a porous sponge or pad as described in U.S. Pat. No. 4,141,359 to Jacobsen et al., and a pre-formed gel body as described in U.S. Pat. No. 4,383,529 to Webster, among others. The pertinent portions of which are incorporated herein by reference. Such reservoirs are electrically connected to, and positioned between, the anode or the cathode and the body surface, e.g., to provide a fixed or renewable source of one or more drugs in the case of agent delivery. In addition, electrotransport systems also typically have an electrical power source, e.g., one or more batteries, and an electrical controller designed to regulate the timing, amplitude and/or frequency of the applied electric current, and hence regulate the timing and rate of agent delivery/sampling. This power source component is electrically connected to the two electrodes. Optional electrotransport device components include a counter reservoir, adhesive coatings, insulating separation layers, and rate-controlling membranes.

FIGS. 1 and 22–25 illustrate a representative electrotransport delivery/sampling device 10 that may be used in conjunction with the present invention. Device 10 comprises an upper housing 16, a circuit board assembly 18, a lower housing 20, anode electrode 22, cathode electrode 24, anode reservoir 26, cathode reservoir 28 and skin-compatible adhesive 30. Upper housing 16 has lateral wings 15 which assist in holding device 10 on a patient's skin. Printed circuit board assembly 18 comprises an integrated circuit 19 coupled to discrete components 40 and battery 32. Circuit board assembly 18 is attached to housing 16 by posts (not shown in FIG. 1) passing through openings 13a and 13b, the ends of the posts being heated/melted in order to heat stake the circuit board assembly 18 to the housing 16. Lower housing 20 is attached to the upper housing 16 by means of adhesive layer 30, the upper surface 34 of adhesive layer 30 being adhered to both lower housing 20 and upper housing 16 including the bottom surfaces of wings 15. Shown (partially) on the underside of circuit board assembly 18 is a button cell battery 32. Other types of batteries may also be employed to power device 10 depending on the need.

The device 10 is generally comprised of battery 32, electronic circuitry 19,40, electrodes 22,24, drug/receptor reservoir 26, counter reservoir 28, and device 2, all of which are integrated into a self-contained unit. The outputs (not shown in FIG. 1) of the circuit board assembly 18 make electrical contact with the electrodes 24 and 22 through openings 23,23' in the depressions 25,25' formed in lower housing 20, by means of electrically conductive adhesive strips 42,42'. Electrodes 22 and 24, in turn, are in direct mechanical and electrical contact with the top sides 44',44 of drug reservoirs 26 and 28. The bottom side 46 of drug reservoir 28 contacts the patient's skin through the opening 29 in adhesive layer 30. The bottom side 46' of drug reservoir 26 contacts the patient's skin through the plurality of openings 8 in the device 2. The formulation of reservoir 26 is preferably a viscous gel that fills the openings 8 such that the reservoir 26 is in direct contact with the skin when the blades have penetrated the stratum corneum. The contact between the reservoir and skin provides a path for the agent to be transported along. If the reservoir 26 is not in direct contact with the skin initially, typically sweat accumulates in the confined area and provides an agent-transmitting pathway between reservoir 26 and the skin.

Device 10 optionally has a feature which allows the patient to self-administer a dose of drug, or self-sample a body electrolyte, by electrotransport. Upon depression of push button switch 12, the electronic circuitry on circuit board assembly 18 delivers a predetermined DC current to the electrode/reservoirs 22,26 and 24,28 for an interval of predetermined length. The push button switch 12 is conveniently located on the top side of device 10 and is easily actuated through clothing. A double press of the push button switch 12 within a short time period, e.g., three seconds, is preferably used to activate the device, thereby minimizing the likelihood of inadvertent actuation of the device 10. Preferably, the device transmits to the user a visual and/or audible confirmation of the onset of operation by means of LED 14 becoming lit and/or an audible sound signal from, e.g., a "beeper". Agent is delivered/sampled through the patient's skin, e.g., on the arm, by electrotransport over the predetermined interval. Anodic electrode 22 is preferably comprised of silver and cathodic electrode 24 is preferably comprised of silver chloride. Both reservoirs 26 and 28 are preferably comprised of polymeric gel materials. Electrodes 22,24 and reservoirs 26,28 are retained by lower housing 20.

In the case of therapeutic agent (i.e., drug) delivery, a liquid drug solution or suspension is contained in at least one of the reservoirs 26 and 28. Drug concentrations in the range of approximately $1 \times 10^{-4}$ M to 1.0 M or more can be used, with drug concentrations in the lower portion of the range being preferred.

The push button switch 12, the electronic circuitry on circuit board assembly 18 and the battery 32 are adhesively "sealed" between upper housing 16 and lower housing 20. Upper housing 16 is preferably composed of rubber or other elastomeric material, e.g., injection moldable ethylene vinyl acetate. Lower housing 20 is preferably composed of a plastic or elastomeric sheet material (e.g., polyethylene) which can be easily molded to form depressions 25,25' and cut to form openings 23,23'. The assembled device 10 is preferably water resistant (i.e., splash proof) and is most preferably waterproof. The system has a low profile that easily conforms to the body, thereby allowing freedom of movement at, and around, the wearing site. The reservoirs 26 and 28 are located on the skin-contacting side of the device 10 and are sufficiently separated to prevent accidental electrical shorting during normal handling and use.

The device 10 adheres to the patient's body surface (e.g., skin) by means of an adhesive layer 30 (which has upper adhesive side 34 and body-contacting adhesive side 36) and the anchoring elements on the device 2 of any of the embodiments discussed above. The adhesive side 36 covers the entire underneath side of the device 10 except where the device 2 and reservoir 28 are located. The adhesive side 36 has adhesive properties which assures that the device 10 remains in place on the body during normal user activity, and yet permits reasonable removal after the predetermined (e.g., 24-hour) wear period. Upper adhesive side 34 adheres to lower housing 20 and retains the electrodes and reservoirs within housing depression 25,25' as well as retains device 2 to lower housing 20 and lower housing 20 to upper housing 16.

In one embodiment of the drug delivery or sampling device there is a bandage cover (not shown) on the device 10 for maintaining the integrity of the device when it is not in use. In use, the bandage cover is stripped from the device before the device is applied to the skin.

Figure 26:
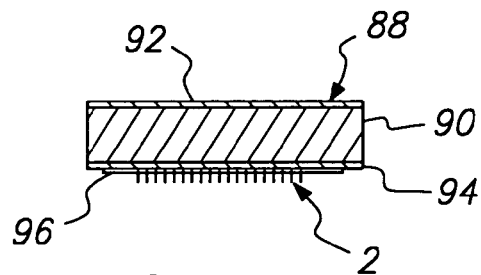
FIG. 26 is a diagrammatic cross-sectional view of a passive agent delivery system in accordance with one embodiment of the present invention.
Figure 27:
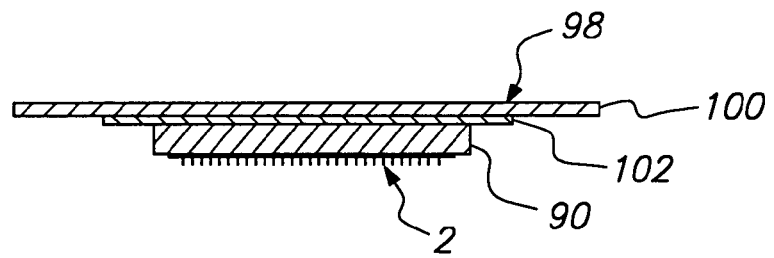
FIG. 27 is a diagrammatic cross-sectional view of another embodiment of a passive agent delivery system in accordance with the present invention.

In other embodiments of the present invention, passive transdermal delivery or sampling devices are used with device 2. Two examples of passive transdermal delivery or sampling devices are illustrated in FIGS. 26 and 27. In FIG. 26, passive transdermal delivery device 88 comprises a reservoir 90 containing agent. Reservoir 90 is preferably in the form of a matrix containing the agent dispersed therein. Reservoir 90 is sandwiched between a backing layer 92, which is preferably impermeable to the agent, and a rate-controlling membrane 94. In FIG. 26, the reservoir 90 is formed of a material, such as a rubbery polymer, that is sufficiently viscous to maintain its shape. If a lower viscosity material is used for reservoir 90, such as an aqueous gel, backing layer 92 and rate-controlling membrane 94 would be sealed together about their periphery to prevent leakage. In a sampling configuration, the reservoir 90 would initially not contain the agent. Located below membrane 94 is microblade array device 2. The device 88 adheres to a body surface by means of contact adhesive layer 96 around the periphery of the device 2 and by the anchoring elements of any of the embodiments described previously. The adhesive layer 96 may optionally contain agent. A strippable release liner (not shown) is normally provided along the exposed surface of adhesive layer 96 and is removed prior to application of device 10 to the body surface.

Alternatively, as shown in FIG. 27, transdermal therapeutic device 98 may be attached to a body surface by means of a flexible adhesive overlay 100 and the anchoring elements used in device 2. Device 98 is comprised of an agent-containing reservoir 90 (for a delivery configuration) which is preferably in the form of a matrix containing the agent dispersed therein. In a sampling configuration, the reservoir 90 would initially not contain the agent. An impermeable backing layer 102 is provided adjacent one surface of reservoir 90. Adhesive overlay 100 maintains the device 98 on the body surface in combination with the anchoring elements of any of the embodiments previously described for device 2. Adhesive overlay 100 can be fabricated together with, or provided separately from, the remaining elements of the device 98. With certain formulations, the adhesive overlay 100 may be preferable to the contact adhesive 96 shown in FIG. 26. This is true, for example, where the agent reservoir contains a material (such as, for example, an oily surfactant permeation enhancer) which adversely affects the adhesive properties of the contact adhesive layer 96. Impermeable backing layer 102 is preferably slightly larger than reservoir 90, and in this manner prevents the agents in reservoir 90 from adversely interacting with the adhesive in overlay 100. Optionally, a rate-controlling membrane (not shown in FIG. 27) similar to membrane 94 in device 88 (FIG. 26) can be provided on the skin/mucosa side of reservoir 90. A strippable release liner (not shown) is also normally provided with device 98 and is removed just prior to application of device 98 to the body surface.

The formulation for the passive transdermal devices may be aqueous or non-aqueous based. The formulation is designed to deliver the drug at the necessary fluxes. Aqueous formulations typically comprise water and about 1 to 2 weight percent of a hydrophilic polymer as a gelling agent, such as hydroxyethylcellulose or hydroxypropylcellulose. Typical non-aqueous gels are comprised of silicone fluid or mineral oil. Mineral oil-based gels also typically contain 1 to 2 weight percent of a gelling agent such as colloidal silicon dioxide.

The reservoir matrix should be compatible with the delivered agent, any excipients (e.g., flux enhancers, irritation preventing agents) and/or any carrier therefore. When using an aqueous-based system, the reservoir matrix is preferably a hydrophilic polymer, e.g., a hydrogel. When using a non-aqueous-based system, the reservoir matrix is preferably composed of a hydrophobic polymer. Suitable polymeric matrices are well known in the transdermal drug delivery art.

When a constant drug delivery rate is desired, the drug is present in the matrix or carrier at a concentration in excess of saturation, the amount of excess being a function of the desired length of the drug delivery period of the system. The drug may, however, be present at a level below saturation without departing from this invention.

In addition to the drug, the matrix or carrier may also contain dyes, pigments, inert fillers, permeation enhancers, excipients and other conventional components of pharmaceutical products or transdermal devices known in the art.

The amount of drug present in the reservoir and the size of the reservoir is generally non-limited and is an amount equal to or larger than the amount of drug that, in its released form, is effective in bringing about the drugs physiological or pharmacological local or systemic effects.

The preferred form in which an agent is delivered or sampled generally determines the type of delivery or sampling system to be used, and vice versa. That is, the selection of a "passive" system which delivers or samples the agent by diffusion or an electrically powered system which delivers or samples the agent by electrotransport will be mostly determined by the form of the agent. For example, with passive delivery systems, it has generally been recognized that the agent is preferably delivered in either its free base or acid form, rather than in the form of a water soluble salt. On the other hand, with electrotransport delivery devices, it has been recognized that the drugs should preferably be ionized and the drug salt should be soluble in water. It is generally believed that the pathways for passive and electrotransported transdermal drug delivery through intact skin are different, with passive delivery occurring through lipid regions (i.e., hydrophobic regions) of the skin and electrotransport delivery occurring through hydrophilic pathways or pores such as those associated with hair follicles and sweat glands. For the case of pierced skin, there is substantial passive flux through the microslits created by the microblades piercing the stratum corneum. The drug for passive delivery is generally hydrophobic, e.g., free base form, whereas the preferred form of a drug for electrotransport delivery is hydrophilic, e.g., water soluble salt form. For osmotic and pressure driven systems which deliver or sample drugs by connective flow carried by a solvent, the drug preferably has sufficient solubility in the carrier solvent. It will be appreciated by those working in the field that the present invention can be used in conjunction with a wide variety of osmotic delivery or sampling systems, as the invention is not limited to a particular device in this regard. Osmotic devices are disclosed for example in U.S. Pat. No. 4,340,048 to Eckenhoff, U.S. Pat. No. 4,655,766 to Theeuwes et al., and U.S. Pat. No. 4,753,651 to Eckenhoff, the disclosures of which are incorporated by reference herein in their entirety.

This invention has utility in connection with the delivery of drugs within any of the broad class of drugs normally delivered through body surfaces and membranes, including skin. In general, this includes drugs in all of the major therapeutic areas including, but not limited to, anti-infectives such as antibiotics and antiviral agents, analgesics including fentanyl, sufentanil, buprenorphine and analgesic combinations, anesthetics, anorexics, antiarthritics, antiasthmatic agents such as terbutaline, anticonvulsants, antidepressants, antidiabetic agents, antidiarrheals, antihistamines, anti-inflammatory agents, antimigraine preparations, antimotion sickness preparations such as scopolamine and ondansetron, antinauseants, antineoplastics, antiparkinsonism drugs, antipruritics, antipsychotics, antipyretics, antispasmodics, including gastrointestinal and urinary anticholinergics, sympathomimetrics, xanthine derivatives, cardiovascular preparations including calcium channel blockers such as nifedipine, betablockers, beta-agonists such as dobutamine and ritodrine, antiarrythmics, antihypertensives such as atenolol, ACE inhibitors such as ranitidine, diuretics, vasodilators, including general, coronary, peripheral and cerebral, central nervous system stimulants, cough and cold preparations, decongestants, diagnostics, hormones such as parathyroid hormone, bisphosphoriates, hypnotics, immunosuppressives, muscle relaxants, parasympatholytics, pasympathomimetrics, prostaglandins, psychostimulants, sedatives and tranquilizers. The invention is also useful in conjunction with reducing or preventing sensitization occurring as a result of electrotransport delivery of proteins, peptides and fragments thereof, whether naturally occurring, chemically synthesized or recombinantly produced. The invention may additionally be used in conjunction with the delivery of nucleotidic drugs, including oligonucleotide drugs, polynucleotide drugs, and genes.

The present invention has particular utility in the delivery of peptides, polypeptides, proteins, nucleotidic drugs, and other such species through body surfaces such as skin. These substances typically have a molecular weight of at least about 300 daltons, and more typically have a molecular weight of at least about 300 to 40,000 daltons. Specific examples of peptides and proteins in this size range include, without limitation, LHRH, LHRH analogs such as goserelin, buserelin, gonadorelin, napharelin and leuprolide, GHRH, GHRF, insulin, insultropin, calcitonin, octreotide, endorphin, TRH, NT-36 (chemical name: N-[[(s)-4-oxo-2-azetidinyl]carbonyl]-L-histidyl-L-prolinamide), lypressin, pituitary hormones (e.g., HGH, HMG, desmopressin acetate, etc), follicle luteoids, $\alpha$ANF, growth factors such as growth factor releasing factor (GFRF), $\beta$MSH, GH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, HCG, hirulog, hyaluronidase, interferon, interleukins, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, bradykinin antagonists, ceredase, CSI's, calcitonin gene related peptide (CGRP), enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonists analogs, alpha-1 antitrypsin (recombinant), and TGF-beta.

Figure 28:
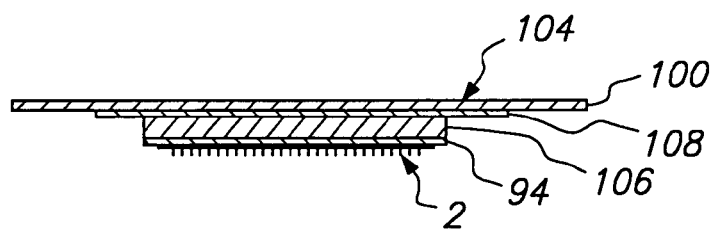
FIG. 28 is a diagrammatic cross-sectional view of a sampling system in accordance with one embodiment of the present invention.

As mentioned above, the device 2 of the present invention can also be used with known sampling devices including, but not limited to, reverse iontophoresis, osmosis, passive diffusion, phonophoresis, and suction (i.e., negative pressure). FIG. 28 illustrates an osmotic sampling device 104 in combination with any of the embodiments described previously for device 2. Osmotic sampling devices can be used to sample any of a variety of agents (e.g., body analytes, licit and illicit drugs) through a body surface including, but not limited to glucose, body electrolytes, alcohol, blood gases, and illicit substances such as drugs of abuse. The osmotic sampling device 104 is attached to a body surface by means of a flexible adhesive overlay 100 and the anchoring elements of device 2. Device 104 is comprised of a salt layer 106 located between a semi-permeable or osmotic membrane 94 and an optional agent sensing element 108. The optional agent sensing element can be any of a variety of chemically reactive sensors and indicators, for example the color indicating test strips associated with glucose testing. The adhesive overlay 100 can have a cut-out or transparent window in the area of the indicators so that the indicators can be readily viewed. In an alternate embodiment, the agent sensing element can be located between the device 2 and the salt layer.

The following example is merely illustrative of the present invention and should not be considered as limiting the scope of the invention in any way, as this example and other equivalents thereof will become apparent to those versed in the art and in light of the present disclosure, drawings, and the accompanying claims.

EXAMPLE

The effect of the present design was evaluated on the skin resistance of a hairless guinea pig. A microblade array of two square centimeters was applied to ECG electrodes of five square centimeters. The blade array and electrodes were then applied to the skin of the animal. Resistance measurements were taken two minutes after application of the electrode to the skin of the animal. A decrease in resistance was observed indicating that penetration of the blades into the skin had occurred.

The device was evaluated for its effect on electrotransport flux of a decapeptide in the hairless guinea pig. The following are specifications for the device: the device consisted of a sheet having a plurality of rectangular openings having six blades, three on each long side of a 860 µm by 250 µm rectangle resulting in a 0.22 mm$^2$ open area for each opening. Each set of three blades started at the opposite end of the rectangle as the opposing set of blades. All of the blades were about 200 µm long. All six blades had slanted leading edges and the blade at each end was barbed as well. The group of six blades were arranged in two slightly offset rows with ten groups in each row on the sheet. Each device was a two cm$^2$ piece of stainless steel 25 µm thick etched and punched with eight pairs of offset rows or 160 groups of six blades for a total of 960 blades. There were 40 void areas per cm$^2$ and 240 blades per cm$^2$.

For the study, a one compartment electrotransport system was used. It consisted of a cathode compartment containing a Dulbelco's phosphate buffered saline imbibing gel and a donor anode compartment containing two millimoles of decapeptide buffered at pH 7.5, 10% cholestyramine chloride and 3% hydroxyethylcellulose. After loading the gels in the system, the release liner was removed from the adhesive foam bottom of the electrotransport system. The device was carefully applied over a 1.6 cm diameter hole containing the donor gel with the microblades facing away from the gel. The electrotransport system was then placed on the skin of a lightly anesthetized hairless guinea pig. The systems were applied to the backs of the animals using gentle downward pressure while at the same time pushing bottom side of the system with the thumb of the technician. (The thumb trapped a roll of the animals' skin which allowed some upward pressure to be applied directly to the bottom side of the skin in contact with the device microblades). After two minutes the current and resistance measurements were observed and recorded. The electrotransport system was wrapped with Vetrap and the animals were returned to their cages for the duration of electrotransport (5 and 24 hours). Decapeptide flux was evaluated by measuring urinary excretion of this peptide. Only a modest effect of the device on decapeptide flux was observed in the first five hours of transport. Between five and twenty-four hours, the electrotransport flux of an ordinary electrotransport device dropped very significantly probably due to collapse of the pathways or possibly aggregation of the peptide in the pathways (the decrease in flux between five and twenty-four hours was reproducible). Use of the blade array device completely prevented this decrease in flux and resulted in an overall ten-fold increase in decapeptide flux over a twenty-four hour transport period.

While the invention has been described in conjunction with the preferred specific embodiments thereof, it is to be understood that the foregoing description as well as the example are intended to illustrate and not limit the scope of the invention. Other aspects, advantages and modifications within the scope of the invention will be apparent to those skilled in the art to which the invention pertains.

The invention claimed is:

1. A device for piercing the stratum corneum of a body surface to form pathways through which an agent can be introduced or withdrawn, comprising a sheet having a least one opening therethrough and a plurality of blades extending downward therefrom, an adhesive anchor applied to at least one surface of said sheet, wherein said adhesive anchor helps prevent said sheet from being dislodged from said body surface, and an agent delivery or sampling device connected to said sheet and positioned to deliver or sample an agent through said opening, said agent delivery or sampling device being selected from the group consisting of an electrotransport device, a passive diffusion device, an osmotic device, and a pressure driven device, and wherein a plurality of blades has a substantially identical and uniform configuration.

2. The device of claim 1, wherein said agent comprises a polypeptide or protein.

3. The device of claim 1, further comprising at least one additional anchoring means selected from the group consisting of a projection extending out from at least one blade of said plurality of blades, a barb, at least one opening extending through said plurality of blades, each one of the plurality of blades defines essentially a plane and wherein said additional anchoring means comprises a portion of said plurality of blades being oriented at an angle of about 90° with respect to a remaining portion of said plurality of blades, and wherein each one of said plurality of blades defines essentially a plane and wherein said additional anchoring means comprises a portion of said plurality of blades being oriented at an angle within a range of about 10° to about 89° with respect to a remaining portion of said plurality of blades.

4. The device of claim 3, wherein said projection extends out from a plane defined by at least one blade.

5. The device of claim 1, wherein said anchor is integral with an edge of said plurality of blades and in a plane defined by said plurality of blades.

6. The device of claim 1, wherein a portion of said blades are located along a periphery of an opening through said sheet.

7. The device of claim 1, wherein a portion of said blades are located along peripheries of a plurality of openings through said sheet.

8. The device of claim 1, further comprising a plurality of second openings through said sheet.

9. The device of claim 1, wherein said device has a blade density of about 600 to about 1000 blades/cm$^2$.

10. The device of claim 1, wherein said device has a blade density of at least about 800 blades/cm$^2$.

11. The device of claim 1, wherein at least a portion of said blades has a length sufficient to pierce the stratum corneum of said body surface to a depth of at least about 25 µm.

12. The device of claim 1, wherein said blades are oriented approximately perpendicular to said sheet.

13. The device of claim 1, wherein said blades are oriented at an angle in a range of about 10° to about 89° to said sheet.

14. The device of claim 1, wherein said blades are oriented at an angle in a range of about 10° to about 60° to said sheet.

15. The device of claim 1, wherein at least a portion of said blades have a thickness in a range of about 7 μm to about 100 μm.

16. The device of claim 1, wherein at least a portion of said blades have a thickness in a range of about 25 μm to about 500 μm.

17. The device of claim 1, wherein said blades are composed of a material selected from the group consisting of metals, metal alloys, glasses, ceramics and rigid polymers.

18. The device of claim 1, wherein said sheet and said blades are substantially impermeable to passage of said agent.

19. The device of claim 1, wherein said blades are thinner than said sheet.

20. The device of claim 1 wherein said sheet has openings per unit area in a range of at least about 10 openings/cm$^2$ to about 1000 openings/cm$^2$.

21. The device of claim 20 having a blade density per unit area in a range of about 10 blades/cm$^2$ to about 1000 blades/cm$^2$.

22. The device of claim 21 wherein said blade density per unit area is in a range of about 600 blades/cm$^2$ to about 1000 blades/cm$^2$.

23. The device of claim 22 wherein said blade density per unit area is in a range of about 800 blades/cm$^2$ to about 1000 blades/cm$^2$.

24. The device of claim 1, having a percolation area in a range of about 0.005 to 0.05 cm$^2$/cm$^2$ of body surface.

* * * * *

UNITED STATES PATENT AND TRADEMARK OFFICE
CERTIFICATE OF CORRECTION

PATENT NO. : 7,184,826 B2  
APPLICATION NO. : 08/877155  
DATED : February 27, 2007  
INVENTOR(S) : Michel J.N. Cormier et al.

Page 1 of 1

It is certified that error appears in the above-identified patent and that said Letters Patent is hereby corrected as shown below:

IN THE TITLE:

Item [54]  
Please delete: "DEVICE AND METHOD FOR ENHANCING TRANSDERMAL FLUX OF AGENTS BEING DELIVERED OR SAMPLED"

and;

Insert : --DEVICE WITH ANCHORING ELEMENTS FOR TRANSDERMAL DELIVERY OR SAMPLING OF AGENTS--

Signed and Sealed this

Twelfth Day of June, 2007

JON W. DUDAS  
*Director of the United States Patent and Trademark Office*